United States Patent [19]

Blades

[11] 4,304,996

[45] Dec. 8, 1981

[54] WATER STERILIZER AND ORGANIC MATTER MEASUREMENT INSTRUMENT

[75] Inventor: Frederick K. Blades, Boulder, Colo.

[73] Assignee: Pure Cycle Corporation, Boulder, Colo.

[21] Appl. No.: 138,695

[22] Filed: Apr. 9, 1980

[51] Int. Cl.³ .............................................. G01J 1/42
[52] U.S. Cl. ................................... 250/373; 250/435; 250/455
[58] Field of Search ................... 250/372, 373, 432 R, 250/435, 455; 356/51, 246, 409, 436, 442; 422/24

[56] References Cited

U.S. PATENT DOCUMENTS

| | | | |
|---|---|---|---|
| 3,465,753 | 9/1969 | Levy et al. ...................... | 250/373 X |
| 3,491,234 | 1/1970 | Wiltrout ............................... | 250/373 |
| 3,535,044 | 10/1970 | Seward ............................... | 356/409 |
| 3,562,520 | 2/1971 | Hippen ............................... | 250/372 |
| 3,566,105 | 2/1971 | Wiltrout et al. ..................... | 250/373 |
| 3,751,167 | 8/1973 | Claus ..................................... | 356/51 |
| 4,103,167 | 7/1978 | Ellner .............................. | 250/373 X |

*Primary Examiner*—Davis L. Willis
*Attorney, Agent, or Firm*—Woodcock, Washburn, Kurtz, Mackiewicz & Norris

[57] ABSTRACT

A combined instrument for the determination of the quantity of organic material present in a water sample is disclosed which features a first photosensor adapted to regulate the output of a source of ultraviolet regulation at a constant level and a second substantially identical photosensor positioned so as to view the same portion of the source of ultraviolet radiation as the first photosensor. The second photosensor produces a signal proportional to the transmittance of the ultraviolet radiation through the water sample and hence inversely proportional to the amount of organic material contained within the water. Such an instrument is also disclosed in combination with a water sterilizer in which the same source of ultraviolet radiation used as to monitor the amount of organic material present in the water is also arranged to provide ultraviolet radiation to the water or provide a bactericidal and sterilizing effect to the water.

10 Claims, 3 Drawing Figures

WATER STERILIZER AND ORGANIC MATTER MEASUREMENT INSTRUMENT

FIELD OF THE INVENTION

The present invention relates to apparatus for measurement of dissolved organic matter in a fluid and for the controlled sterilization of the fluid. More particularly, a method and instrument is disclosed for continuous measurement of dissolved organics in water using short wave ultraviolet (UV) radiation from a low-cost germicidal lamp; in accordance with a further aspect of the invention, the UV lamp may additionally serve as a source of sterilization of water by exposure of bacteria and other living organic matter to ultraviolet radiation.

BACKGROUND OF THE INVENTION

In accordance with the recent emphasis on improved availability of potable water, and the more stringent drinking water standards instituted by the Environmental Protection Agency (EPA), the need has increased for an economical method of continuously monitoring the organic content of a stream of process water as a measure of its purity.

One conventional method, using the oxidation of carbon to carbon dioxide and measurement of the carbon dioxide, yields a direct measure of the total organic carbon (T.O.C.), but involves unwieldy procedures requiring specially trained operators. As a result, this general approach is costly and not readily adaptable to continuous measurements. Furthermore, this method provides a measurement of all the carbon in the sample, so that additional steps are required to limit the measurement to the dangerous organic carbon.

Another method, utilizing biochemical oxygen demand (BOD) determination, involves seeding and incubation of a discrete sample for a standard 5 day period, and is accordingly entirely unsuitable to real-time processing.

Yet another method utilizing chemical oxygen demand (COD) determination involves elaborate laboratory procedures, entailing reagent supply and waste disposal problems, and is far too elaborate for ready use.

In addition to the defects noted, all these methods have relatively low sensitivity and are subject to operator errors. The present invention exploits the well known fact that organic compounds, particularly those having aromatic or conjugated unsaturated molecular configurations, absorb UV radiation in the region of 2000–3000 Å; therefore, by measuring UV absorbtion, these compounds can be measured. For example, it has been shown empirically by H. Tinsley & Co., Ltd., that there is good correlation between UV absorption measurements and the total organic carbon (TOC) in both river water and sewage effluents; effluents having high mineral contents may differ. Studies at the Mellon Institute in Pittsburgh have shown that such measurements can discern trace organic compounds likely to cause taste and odors in drinking water; see Bramer et al, Instrument for Monitoring Trace Organic Compounds in Water, *Water & Sewage Works*, Aug. 1966, pp. 275–278.

Such measurements are particularly useful in measuring trace organics in the output of sewage treatment systems, where deionization and filtration steps are provided to remove non-organic compounds likely to interfere with the measurements such as minerals, which also absorb UV radiation. In such situations, an order of magnitude better resolution can be achieved than with chemical methods of TOC measurement.

Devices are known which employ UV absorption measurements to yield a measure of the dissolved organics. One such instrument, described in U.S. Pat. No. 3,751,167 issued to George Claus Feb. 23, 1971, passed filtered UV radiation directly through a cuvette containing the sample fluid to a UV responsive photosensor. Such a device is subject to significant drift with age due to fouling and solarization of the cuvette windows, varying source intensity (a particularly difficult problem with inexpensive germicidal lamps) and gradual degradation of the reflectivity of the internal surfaces.

Another device, described in U.S. Pat. No. 3,535,044 issued to H. Seward, Oct. 20, 1970, utilizes a reference sensor in direct view of the source, thus providing a non-attenuated signal which can be used to compensate for variations in source intensity. However, this approach does not solve problems connected with the sample chamber, such as solarization of the sample tube windows, and reflectivity of the instrument's internal surfaces, nor those connected with the stability of the temperature. Nor does Seward show a suitable sensor.

Yet another device, produced by H. Tinsley & Co., Ltd. similar to that described in the Bramer et al paper referred to above, splits the radiation having been transmitted through the sample into visible and UV components, and provides an output proportional to the ratio of the absorbance of the ultraviolet radiation to that of the visible light. Though this approach is effective in rejecting turbidity of the sample as a contributor to UV absorbtion, variations in the UV intensity relative to that of the visible intensity from the source would not be compensated for; a particular problem in mercury lamps, in which the UV/visible ratio varies dramatically with bulb temperature and age. Moreover, solarization of the windows affects only the UV transmission, thus introducing additional errors.

A further problem encountered arises from the unstability and flicker of the arc lamps generally used on such instruments. Both the Seward and the Tinsley devices utilize pulsed measurement techniques to minimize this problem. Despite their inherent instabilities, arc lamps, particularly the low-pressure mercury vapor variety known as germicidal lamps, are an inexpensive and useful source of short-wave UV radiation. With an output consisting primarily of 253.7 nm, such lamps have found wide application in sterilizers and the like.

Devices are known which employ sensors to measure the UV transmittance of the fluid and thereby activate various devices to render the system fail-safe. One such device is described in U.S. Pat. No. 3,566,105 issued to D. Wilhout on Aug. 16, 1968. The Wilhout device uses a UV responsive photodetector mounted on the wall of the fluid container, illuminated by the lamp radiation through the liquid. A similar device is described in U.S. Pat. No. 3,562,520 issued to R. Hippen on Nov. 4, 1968. Devices of this nature are subject to contamination of the sensor surface and solarization of the sensor itself, and are limited in resolution. Therefore, a need exists in the art for an improved ultraviolet transmittance sensor for monitoring the amount of organic material in a fluid sample.

As discussed above, sterilization by UV exposure from a germicidal lamp is a commonly used method for disinfecting fluids by killing all bio-organisms such as viruses and bacteria without the need for added chemicals. In such systems, the efficiency of the sterilization process is a function of the exposure intensity and duration. Therefore, fouling, solarization, and aging of the UV source and its enclosure as well as changes in the absorption characteristics of the fluid can severely degrade the performance of the sterilizer. Moreover, such a reduction in efficiency is often not apparent since the source, if a conventional lamp, may continue to emit visible light. Further, it will be understood that variations in lamp intensity due to aging, line voltage variation and temperature will also affect the reading accuracy. Since a minimum amount of sterilization is required, over the life of the lamp, the prior practice is to supply excess power, sometimes as much as 50% to the lamp when new, thus wasting energy, reducing the usable life of the lamp, and aggravating the aging problem. A need therefore exists in the art for means to accurately measure the UV output of a UV source, and to control it at a constant level.

OBJECTS OF THE INVENTION

It is therefore an object of the present invention to provide an improved method for the measurement of low-level dissolved organics in fluid.

A further object of the invention is to provide an economical, reliable, accurate and sensitive instrument for the continuous measurement of dissolved organics in water.

A still further object is to provide an instrument for the measure of absorbed organics in water, utilizing a low cost germicidal lamp.

Yet another object of the present invention is to provide a sterilizer with an improved means to regulate and monitor the sterilization efficiency.

Still another object is to provide an apparatus using a single ultraviolet source for the simultaneous sterilization and continuous measurement of dissolved organics in liquids.

SUMMARY OF THE INVENTION

In accordance with the needs of the art and the objects listed above, the invention provides an instrument for the continuous monitoring of dissolved organics in fluids. Further, the remaining radiation from the instrument UV source may be used to provide a controlled amount of UV radiation for sterilization purposes.

Thus, in accordance with the present invention, a single germicidal lamp serves as a source for both sterilization and measurement purposes. A first photosensor, selectively responsive to the primary emission line (substantially 254 nm) of the germicidal lamp is positioned to view a small section of one side of the lamp through a short length of the sampled fluid. The photosensor output controls a high-frequency switching power supply that in turn supplies power to the lamp. Thus, a feedback loop is established which regulates the intensity of the radiation falling on the surface of the first photosensor at a constant value.

A second, substantially similar photosensor is positioned to view the same section of the lamp from its other side through a substantially longer length of the sample fluid. The output of the second photosensor is amplified to produce a signal proportional to the transmittance of the UV radiation, through the difference in path lengths; since this is fixed, a signal proportional to the transmittance and, therefore, the organic content of the fluid may be derived. It will be noted that the reading from the absorption monitor, which is proportional to transmittance, may be used as a measure of the sterilization efficiency. Moreover, since the optical path is largely common to both photosensors, errors due to changes in the path are cancelled. Apertures are included in both paths to minimize errors due to surface reflection variations on the internal chamber walls, and to produce substantially equal amounts of radiation at the surface of both photosensors to cancel errors due to solarization and temperature drift of the sensors. The two photosensors thus being colinear with the sampled or viewed section of the lamp allows variations in the lamp over time to be compensated for automatically without disturbing the accuracy of the reading.

The germicidal lamp regulated by the first photosensor is held at a constant output level of radiation at 254 nm. The remainder of the lamp, which may extend up to several feet on either side of the sensing area, is then available as a controlled source of radiation for sterilization.

DESCRIPTION OF THE PREFERRED EMBODIMENTS

Figure 1:
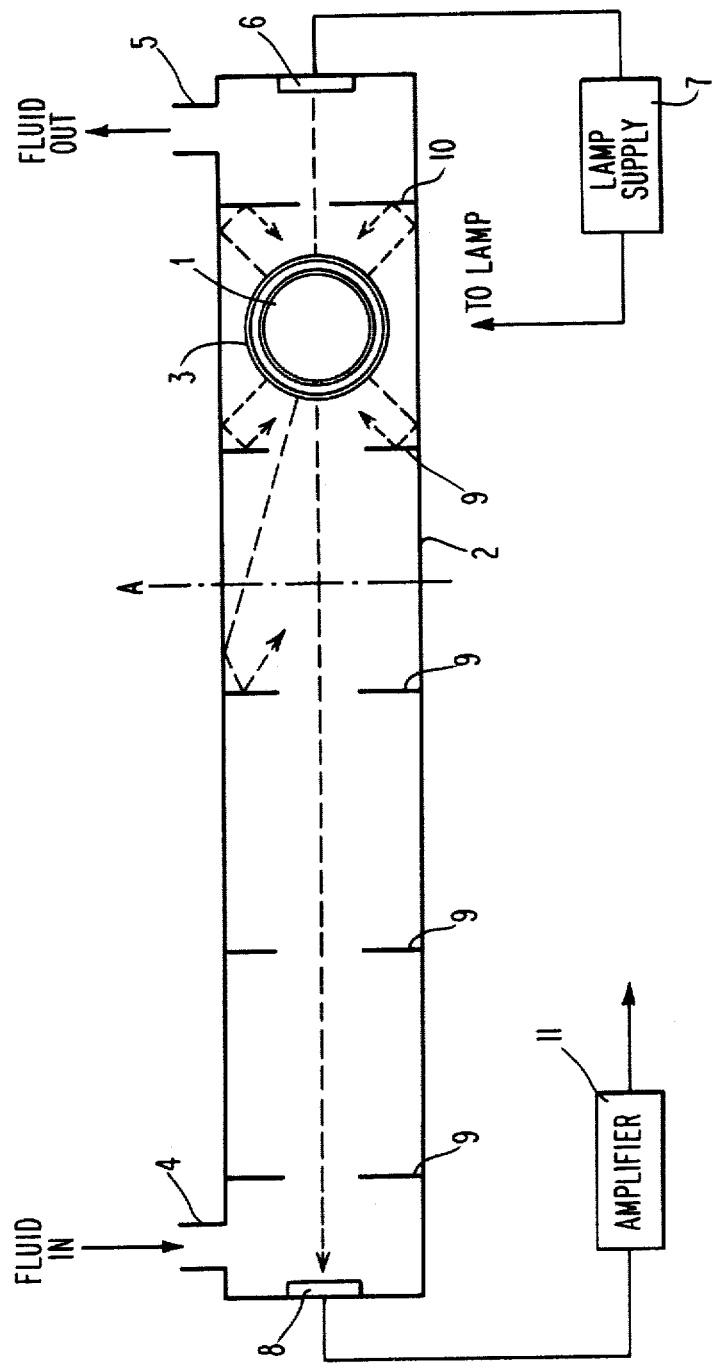
FIG. 1 is a cross-sectional view of an instrument in accordance with the present invention, for the continuous measurement of dissolved organics in a fluid.

Referring now to FIG. 1, a germicidal lamp 1, shown in a radial sectional view, is placed within a fluid chamber 2 and isolated from the fluid to be tested by a protective tube 3. The tube 3, which is of a material essentially transparent to the UV radiation, such as quartz, seals the fluid from the lamp. The fluid enters the input port 4, flows through the chamber 2 and exits through the output port 5.

Radiation from the lamp 1 enters the sample water through the protective tube 3 and illuminates the substantially identical photosensors 6 and 8 which may be characterized broadly as radiation sensitive devices. Both photosensors 6 and 8 are selectively responsive to 254 nm UV radiation when illuminated by radiation from a low pressure mercury-vapor lamp, and are preferably as described in my copending application Ser. No. 80,097, now U.S. Pat. No. 4,272,679 filed Sept. 28, 1979.

The output of the "short side" photosensor 6 controls the power delivered to the bulb via the lamp supply 7 by means of a conventional feedback circuit to precisely maintain the intensity reaching its surface at a constant level. The lamp supply may be a high frequency switching supply adapted to drive an arc lamp, in which regulation is accomplished through pulse width modulation of the power supplied to the lamp.

Since the level of radiation reaching the surface of the "short side" photosensor 6 is held precisely constant, it will be appreciated that the same constant radiation level is maintained at point A, equidistant from the lamp on its other side, regardless of the absorption characteristics of the fluid. This is true because the optical environments are essentially identical; that is, the sample fluid can be assumed to be homogeneous over the length of the chamber 2. Radiation from the lamp proceeds then through the remaining fluid to the "long side" photosensor 8. Therefore, the total radiation reaching the "long side" photosensor 8 is equal to that which is transmitted through the "short side" less that absorbed over the difference in path lengths between the "short side" and the "long side" path length; i.e. from point A to the "long side" photosensor 8. Since the radiation at point A is held constant by regulation of the lamp, the output of photosensor 8 is proportional to the absorption characteristics of the fluid. Most importantly, this signal is not affected by the emission characteristics of the lamp 1.

Baffles 9 positioned in the "long side" optical path serves to minimize reflection from the internal surfaces of the chamber, thus preventing errors from changes in their reflectivity with aging.

A baffle 10 positioned in the "short side" optical path also reduces reflection from the internal surfaces and is sized to reduce the intensity of light reaching the "short side" photosensor 6 to essentially the same level as that reaching the "long side" photosensor 9, to compensate for the attenuation along the long side. In this way, solarization of the two sensors proceeds at the same rate, thus eliminating another possible source of error.

It is appropriate at this time to define the terms "transmittance" and "absorbance" as used herein. "Transmittance" though a sample of fluid is defined as the ratio of the intensity of light incident to a sample of fluid to that transmitted through the sample of fluid:

$$t = I/I_o$$

where
t = transmittance;
I = intensity of light transmitted through the fluid sample; and
$I_o$ = intensity of light incident to the fluid sample.

The absorbence (A) is defined in logarithmic terms such that:

$$A = -\log t = -\log I/I_o$$

and the absorption coefficient $\alpha$ is defined as:

$$\alpha = \frac{-\log I/I_o}{b}$$

where
b = path length or
$I = I_o 10^{-ab}$

To express the operation of the system in mathematical terms we let:
$b_s$ = "short side" path length
$b_L$ = "long side" path length
$I_s$ = intensity of light reaching the surface of the "short side" photosensor 6
$I_L$ = intensity of light reaching the surface of the "long side" photosensor 8
$I_o$ = intensity of light leaving the lamp 1
Thus since:

$$I = I_o 10^{-ab},$$

the intensity of light reaching the "short side" photosensor 6 can be expressed in terms of the absorption coefficient of the fluid sample:

$$I_s = I_o 10^{-abs} \tag{1}$$

and
similarly the intensity reaching the "long side" photosensor 8 is $$I_L = I_o 10^{-abL} \tag{2}$$

Solving for $I_o$ in equation (1) above yields:

$$I_o = I_s 10^{abs}$$

Substituting this expression for $I_o$ into equation (2) gives $$I_L = I_s 10^{abs} 10^{-abL}$$

Thus:

$$I_L = I_s 10^{-a(bL-bs)}$$

or $$\alpha = \frac{\log I_s/I_L}{\Delta b}$$

Where $\Delta b$ is the difference in path lengths ($\Delta b = b_L - b_s$)
or $$A = \log I_s/I_L \tag{3}$$

where A = Absorbance

It can be seen that $I_o$, the intensity of the lamp, is effectively cancelled out. That is, only the difference in path length $\Delta b$ need be defined to yield a true value for the absorbence and hence, the sterility of the sample under test.

Returning now to the discussion of FIG. 1, it will be noted that since both sensors are in essentially identical optical environments and are viewing the same light source (that is, the same segment of the lamp 1) numerous possible sources of inaccuracy due to aging of the system such as discoloration and solarization of the transmissive elements, film deposits and lamp degradation affect both sensors in the same fashion and are thus also effectively cancelled out. Moreover, as the incident radiation is substantially equal on both sensors, as discussed above, the solarization of the two sensors proceeds at essentially the same rate. Solarization can be limited if the sensors are as described in my co-pending application Ser. No. 80,097.

The photosensors 6 and 8 are desirably variable resistance type transducers; their resistance R is inversely proportional to the incident intensity I:

$$I = 1/KR \tag{4}$$

Where K is a constant depending on the nature of the transducer. Since the intensity of radiation reaching the "short side" photosensor is maintained constant due to the regulatory action of the feedback loop, substitution of equation (4) in equation (3) and combining the constants yields a signal proportional to absorbance:

$$A = \log KR_L$$

Where $R_L$ = resistance of the "long side" photosensor 8. Additionally the transmittance is $t = 1/KR_L$ Amplifier 10, for the "long side" photosensor 8, is desirably a transconductance type, gain adjusted to produce an output equal to or proportional to R. With R available, both absorption, f(log R), or transmittance, f(1/R), can readily be derived. R can be measured by analog circuitry known in the prior art (e.g. Wheatstone bridge circuitry) to provide a continuous indication of either transmittance or absorbance.

In other applications it may be desirable to perform the processing through digital means such as with a microprocessor control system, to activate or deactivate various devices at certain preset levels of transmittance or absorbance of the fluid; see, e.g. U.S. Pat. No. 4,145,279 to Selby, which describes a water recycle system with which the present invention is useful. In that system, carbon absorber means is provided to absorb organic matter. The output of the instrument of the invention is accordingly a measure of the efficacy of the carbon absorption step.

Figure 2:
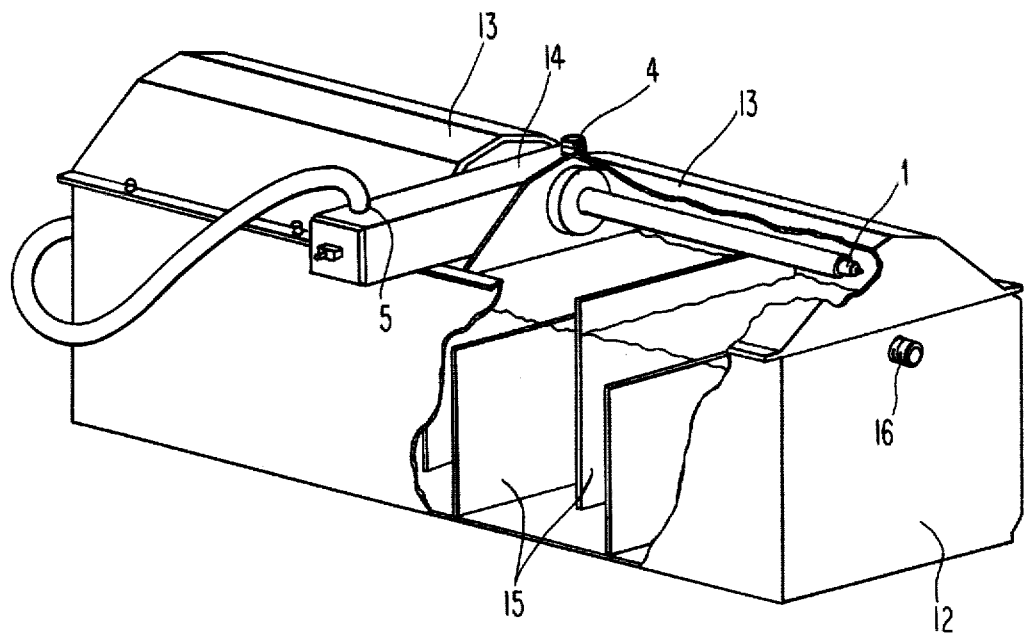
FIG. 2 is a perspective view of one embodiment of a UV sterilizer combined with the instrument illustrated in FIG. 1.

As was stated previously, the lamp 1, shown in radial section in FIG. 1, is desirably a germicidal lamp. Referring now to FIG. 2, it can be seen that the lamp 1 may extend up to several feet on either side of the absorption monitor instrument indicated generally at 14 and described above. Germicidal lamps are commercially available in a wide range of diameters and lengths and can therefore be chosen dependent on the particular requirements of the application.

Referring again to FIG. 2, an embodiment is illustrated which makes use of the additional radiation available for the purpose of sterilization of the fluid.

The absorption monitor instrument 14 is mounted in this embodiment on top of the reservoir 12 which contains the fluid. Fluid enters the absorption monitor assembly 14 via an inlet port 4 and exits via outlet port 5 and passes into the reservoir 12. The reservoir 12 is sized and constructed in such a manner as to allow maximum retention time of the fluid. A reflective cover 13 is provided to contain the radiation and reflect it back down into the fluid. If the reflective cover is made of aluminum, it may desirably be finished by coating it according to the General Electric Co.'s AL-GLAS process. As shown, internal baffles 15 may be provided to cause a particular flow pattern to occur. Thus UV light emitted from the lamp 1 exposes the fluid flowing through the reservoir 12, and thereby sterilizes and disinfects the same. The sterilized and monitored water eventually exits by means of a port 16.

It will be apparent that many advantages are gained from such a configuration over conventional sterilization means. First, the level of radiation emitted from the lamp 1 is held constant to a fluid depth equal to the "short side" path length. Thus as the lamp ages or a film is deposited on its surface, the power delivered to the lamp is increased to compensate. That is, no more than the minimum required power is delivered, thus saving energy and extending bulb life.

Additionally the transmittance can be derived from the output to determine the efficiency of sterilization.

Thus at predetermined levels of sterilizaton efficiency for example, various devices may be activated or deactivated to "fail-safe" the sterilization process. Preferably, in the context of the Selby system referenced above, an indication of excess biomass in the fluid tested results in its being returned to the biological digestion stage of the process.

Figure 3:
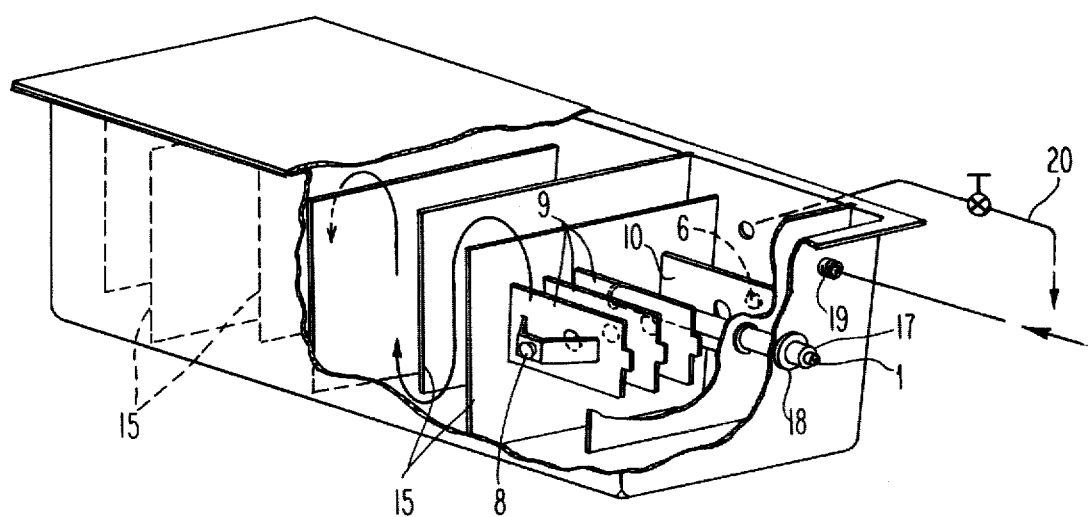
FIG. 3 is a simplified perspective view of another embodiment of a combined sterilizer and instrument for the continuous measurement of dissolved organics.

One problem which can arise with the embodiment of FIG. 2 is that the lamp temperature can vary over its length, due to the monitored section being submerged. This can be alleviated by providing a nichrome heater between the lamp 1 and enclosing tube 3. In an alternate embodiment of the present invention, illustrated in FIG. 3, this problem is eliminated. In this case, the lamp is entirely submerged in the fluid, which is inlet at inlet port 19; short and long side sensors 6 and 8 respectively operate as above, as do aperture plates 9 and 10. A protective tube 17, essentially transparent to the UV radiation, is positioned around the lamp 1 to provide thermal insulation and a convenient means to replace the lamp. The protective tube is mounted and sealed to fluid reservoir end plates 18. The lamp 1 is then free to be positioned in and removed from the protective tube 14.

In this embodiment, the absorption monitor assembly is submerged within the fluid reservoir to eliminate the need for a separate assembly and thus reduce the cost, as well as providing equal temperature to the lamp over its length, thus stabilizing its operation. Again, baffles 15 may be provided to define a long flow path within the chamber 12, so that adequate residence time is ensured. A valve and pipeline 20 may be provided so that if the output of the absorption monitor indicates that sterilization is insufficient, the liquid can be recycled to an earlier part of the system in which the sterilizer is used for reprocessing.

While several preferred embodiments of the invention have been described, numerous modifications can be made thereto without departure from its spirit and scope as defined by the following claims.

What is claimed is:

1. Instrument for measuring the transmission of ultraviolet radiation through a sample of fluid, comprising a first radiation-sensitive device spaced a first short distance from a source of said radiation within said fluid sample and used to control said source such that the intensity of said radiation passing through said sample, and incident on said device remains constant, and a second radiation sensitive device spaced a second, longer distance within said sample from said source, whereby said second radiation sensitive device produces a signal proportional to the transmission of ultraviolet radiation through a distance in said fluid sample equal to the difference between said first and second distances.

2. The instrument of claim 1 wherein said first and second radiation-sensitive devices are colinear and view the same portion of said source, whereby variations in the radiation emitted over the extent of said source are eliminated from affecting said signal.

3. The instrument of claim 1 wherein said radiation is chiefly ultraviolet, having a primary component of wave length 254 nanometers.

4. The instrument of claim 1 wherein said radiation sensitive devices are substantially identical photosensors.

5. The instrument of claim 4 wherein said photosensors are substantially sensitive to ultraviolet radiation and are relatively insensitive to visible light, whereby variation in the ratio of visible to ultraviolet radiation emitted by said source does not affect said signal produced by said second photosensor.

6. The instrument of claim 1 wherein means are provided defining the paths of said radiation extending between said source and said first and second radiation-sensitive devices such that the optical characteristics of said second path differ substantially from those of said first path only as to length.

7. An apparatus for the sterilization of water by exposure of said water to ultraviolet radiation and for monitoring the organic content of said water, comprising a source of ultraviolet radiation for sterilizing said water, a tank for containing said water such that said water is exposed to said radiation for a period sufficient that said radiation exerts a bactericidal effect on said water, first sensor means responsive to ultraviolet radiation for controlling the radiation emitted by said source and incident on said first sensor means at a substantially constant level, and second means responsive to ultraviolet radiation for generating a signal in response thereto proportional to the organic content of said water, wherein said source of ultraviolet radiation for sterilization is also the source of the radiation measured by said means responsive to ultraviolet radiation, wherein the optical paths leading from said source of ultraviolet radiation to said first and second means responsive to ultraviolet radiation are substantially identical except as to length.

8. The apparatus of claim 7 wherein both said means responsive to ultraviolet radiation are substantially similar photosensor means.

9. The apparatus of claim 8 wherein said photosensor means and said source of ultraviolet radiation are positioned such that both said photosensors view the same portion of said source.

10. The apparatus of claim 7 wherein said tank comprises baffles defining a flow path of said water whereby the residence time of said water in said tank is lengthened.

* * * * *